US005744679A

United States Patent [19]

Marinangeli et al.

[11] Patent Number: 5,744,679
[45] Date of Patent: Apr. 28, 1998

[54] USING WATER CONCENTRATION TO CONTROL ETHYLENE OLIGOMERIZATION

[75] Inventors: Richard E. Marinangeli, Arlington Heights; Timothy A. Brandvold, Buffalo Grove, both of Ill.

[73] Assignee: UOP LLC, Des Plaines, Ill.

[21] Appl. No.: 775,051

[22] Filed: Dec. 27, 1996

[51] Int. Cl.[6] .................... C07C 2/08; C07C 2/22; C07C 2/16; C07C 2/18
[52] U.S. Cl. ................ 585/526; 585/502; 585/520; 585/521; 585/523; 585/524; 585/527; 585/530; 585/531; 585/532
[58] Field of Search ................. 585/502, 520, 585/521, 523, 524, 526, 527, 530, 531, 532

[56] References Cited

U.S. PATENT DOCUMENTS

| 3,676,523 | 7/1972 | Mason | 585/526 |
| 4,472,522 | 9/1984 | Singleton | 585/523 |
| 4,689,437 | 8/1987 | Murray | 585/526 |

*Primary Examiner*—Elizabeth D. Wood
*Attorney, Agent, or Firm*—Thomas K. McBride; Eugene I. Snyder

[57] ABSTRACT

Ethylene is effectively oligomerized to linear alpha-olefins using catalyst systems based on transition metal compounds. It has been found that when the reaction is conducted in a polar organic liquid as solvent, incorporation of water into the solvent at levels of 1 to 10 weight percent increases alpha-olefin purity and also influences the Schulz-Flory distribution.

7 Claims, No Drawings

USING WATER CONCENTRATION TO CONTROL ETHYLENE OLIGOMERIZATION

BACKGROUND OF THE INVENTION

Linear olefins are one of the most useful classes of hydrocarbons used as raw materials in the petrochemical industry and among these the linear alpha-olefins—unbranched olefins whose double bond is located at a terminus of the chain—form an important subclass. Linear alpha-olefins can be converted to linear primary alcohols by hydroformylation (oxo synthesis); alcohols of carbon number less than eleven are used in the synthesis of plasticizers whereas those of carbon number greater than eleven are used in the synthesis of detergents. Hydroformylation also can be used to prepare aldehydes as the major products which in turn can be oxidized to afford synthetic fatty acids, especially those with an odd carbon number, useful in the production of lubricants. Linear alpha-olefins also are used in the most important class of detergents for domestic use, namely the linear alkylbenzenesulfonates, which are prepared by Friedel-Crafts reaction of benzene with linear olefins followed by sulfonation.

Another important utilization of alpha-olefins is radical hydrobromination to give primary bromoalkanes which are important intermediates in the production of thiols, amines, amine oxides, and ammonium compounds. Direct sulfonation of the alpha-olefins afford the alpha-olefin sulfonates, a mixture of isomeric alkenesulfonic acids and alkanesulfones, which are effective laundry agents even in hard water and at low concentrations. Linear alpha-olefins, particularly those of eight carbons and under also are used as comonomers in the production of high density polyethylene and linear low density polyethylene.

Although linear olefins are the product of dehydrogenation of linear alkanes, the major portion of such products are the internal olefins. Preparation of alpha-olefins is based largely on oligomerization of ethylene, which has as a corollary that the alpha-olefins produced have an even number of carbon atoms. Oligomerization processes for ethylene are based mainly on organoaluminum compounds or transition metals as catalyst. Using catalytic quantities of, for example, triethylaluminum, the oligomerization of ethylene proceeds at temperatures under 200° C. to afford a mixture of alpha-olefins whose carbon number follows a Schulz-Flory distribution. In the C6–C10 range there is less than 4% branched alpha-olefins, but the degree of branching increases to about 8% as the chain length is extended to the 18. A modified process, the so-called Ethyl process, affords a high conversion of ethylene to alpha-olefins with a more controlled distribution but product quality suffers dramatically, particularly in the content of branched olefins. Thus, in the C14–C16 range linear alpha-olefins represent only about 76% of the product.

A notable advance in the art accompanied the use of transition metals as catalysts for ethylene oligomerization. The use of, for example, nickel, cobalt, titanium, or zirconium catalysts afforded virtually 100% monoolefins with greater than 95% as alpha-olefins, under 3% as branched olefins, and under 3% as internal olefins. Since the catalysts are insoluble in hydrocarbons, oligomerization by catalyst systems based on transition metals typically is performed in a polar solvent to solubilize the catalyst. Ethylene and its oligomers have limited solubility in the polar solvents used, consequently the oligomerization process is associated with a 3-phase system; a polar liquid solvent phase containing the catalyst, a second liquid hydrocarbon phase (consisting of the oligomers produced), immiscible with the polar liquid phase, and ethylene in the vapor phase. Such a system permits a continuous oligomerization process, since ethylene can be introduced into the polar phase and oligomerization products can be withdrawn as the hydrocarbon phase.

Ethylene oligomerization affords alpha-olefins with a Schulz-Flory distribution which is catalyst dependent and, at least for the catalysts of major interest herein, temperature dependent to a lesser degree. Murray recently has described a class of catalysts having a transition metal component particularly attractive as oligomerization catalysts; U.S. Pat. No. 4,689,437, U.S. Pat. No. 4,716,138, and U.S. Pat. No. 4,822,915. See also U.S. Pat. No. 4,668,823. Using such catalysts under conditions where the Schulz-Flory distribution constant is in the range of 0.55–0.65 affords an oligomerization product whose alpha-olefin distribution in the C6–C16 range is particularly desirable from an economic viewpoint. That is, the economic value of ethylene oligomers may be maximized by having a Schulz-Flory distribution of about 0.65. A concomitant of oligomerization at such conditions is the production of about 10% of oligomers having 20 or more carbon atoms (C20+) which are waxy solids at ambient temperature having limited solubility in the hydrocarbon phase of the oligomerization process described above and which tend to separate as waxy solids with concomitant reactor plugging. We recently disclosed a solution for this vexing problem in U.S. Pat. No. 5,523,508.

Linear alpha-olefin formation by oligomerization of ethylene as catalyzed by transition metal salts such as Ni(II) has as its most significant commercial variable the Schulz-Flory distribution constant, α, for this determines the distribution of oligomers formed. Since the requisite oligomer distribution varies with the market into which the products are sold, it is clear that market needs will determine the α of the most economic oligomerization process, hence the supplier will tend to effect the process at the desired α. The Schulz-Flory distribution varies with the ligand used, but varying the ligand to vary α is largely illusory since only a limited number of ligands are themselves commercially viable because of availability, of cost, and of the purity of the ligand itself. The Schulz-Flory distribution also varies somewhat with temperature, but the temperature dependency of α is usually quite small. Thus, the variables which can be used to control α are quite limited in the commercial context and there is a need to introduce further controls into the oligomerization process.

Although the oligomeric olefins formed in a linear alpha-olefin process are largely terminal olefins, significant amounts of branched olefins and internal olefins also are formed as undesirable by-products which lower the value of the product. The linear alpha-olefins are used in detergent manufacture, either by direct sulfonation to alkylsulfonates, or via alkylation of aromatics followed by sulfonation to afford linear alkylbenzenesulfonates. In either case, linearity of the alkyl chain is a critical aspect of biodegradability. Where oligomers are used in, for example, polyethylene formation, the presence of internal oligomers leads to reactivity problems with respect to polyethylene formation; the presence of either branched or internal olefins also leads to subtle differences in properties of the resulting polyethylene, differences which are usually undesirable. Thus, minimization of internal and branched olefins formed via ethylene oligomerization is a high priority in any process.

Consequently it came as a surprise to us to note that when ethylene is oligomerized in a process using transition metal compounds as a catalyst in sulfolane as a solvent, the presence of water affected the process in several ways which could be utilized to improve linear alpha-olefin production. Our observations were unexpected since conventional wisdom held the presence of water was detrimental, and that it was necessary to work with as dry sulfolane as possible. Our observation also is surprising since no such effects were previously noted. What we observed is that water increases the purity of olefinic oligomers to afford more alpha-olefins at the expense of decreased amounts of internal and branched olefins, clearly a quite desirable result. It also was noted that the concentration of water present affected the Schulz-Flory distribution, so that if necessary temperature increases shifted α this shift could be counteracted by increasing the water concentration. Thus, the concentration of water acted as a means of controlling the ethylene oligomerization process. Since the number and the nature of methods of controlling the process are limited, this is a significant addition to the arsenal of process methods.

We also observed that increasing the concentration of water has an adverse effect on oligomer productivity. However, in a system where the catalyst is a transition metal salt and ligands, and where an activator also is employed in conjunction with the catalyst, we made the ancillary observation that such a decrease in productivity can be offset, at least in part, by increasing the catalyst concentration or activator concentration. Thus, the overall effects of adding water to the reaction system are beneficial.

SUMMARY OF THE INVENTION

The purpose of our invention is to increase the purity of ethylene oligomers in an oligomerization process catalyzed by a transition metal catalyst system dissolved in an organic polar solvent. An embodiment comprises adding water to the organic polar solvent in an amount from about 1 to about 10 wt. % of the solvent. In another embodiment the polar solvent contains from about 2 to about 5 wt % water. In yet another embodiment the transition metal catalyst system comprises a transition metal compound, an organophosphorus sulfonate ligand, and optionally (but quite desirably) a catalyst activator. In still another embodiment the polar organic solvent is sulfolane. Other embodiments will be recognized by one of ordinary skill from the description which follows.

DESCRIPTION OF THE INVENTION

We have made the observation, without precedent in the prior art, that the addition of water to a polar organic liquid serving as a solvent for a transition metal catalyst system in a process for oligomerization of ethylene affords higher purity linear alpha-olefin oligomers than those formed in the absence of water. We furthermore have observed that the concentration of water in a polar organic solvent affects the Schulz-Flory distribution of olefinic oligomers resulting from the oligomerization of ethylene. Thus, the concentration of water in a polar organic liquid serving as the solvent provides a measure of control over olefinic oligomer distribution. Although productivity—that is, per pass conversion of ethylene to oligomeric olefins—decreases as water is added to a polar organic solvent, the decrease is counteracted by increasing the concentration of the catalyst system and/or increasing the concentration of the activator.

The process of our invention deals with the oligomerization of ethylene as catalyzed by transition metal catalyst systems. See, for example, Ullman's Encyclopedia of Industrial Chemistry, 5th Ed., V. A13, pp. 245 et. ff., VCH (1989). A particularly desirable transition metal catalyst system is that described by Murray in U.S. Pat. No. 4,689,437, all of which is incorporated herein. The transition metal catalyst system described there is a reaction product of three components; a transition metal compound, a catalyst activator, and an organophosphorus sulfonate ligand. Other transition metal catalyst systems are described in, e.g., U.S. Pat. Nos. 3,635,937, 3,637,636, 3,644,563, 3,644,564, 3,647,915, 3,661,803 and 3,686,159. Since transition metal catalyst systems for ethylene oligomerization are well known in the art they need not be further discussed herein.

Typical catalyst concentrations are in the range of about 10 ppm to about 1,000 ppm of transition metal. Some of the more active catalysts give quite high reaction rates at 40 ppm, and a broader range of catalyst concentration is between about 0.1 to about 1,000 ppm. In a preferred mode of practicing our invention catalyst concentrations range between about 15 and about 300 ppm. We prefer using the catalyst system of Murray as described in U.S. Pat. No. 4,689,437, which is the reaction product of a transition metal compound, a catalyst activator, and an organophosphorus ligand. Nickel is our preferred transition metal, and we have found a borohydride, e.g., sodium borohydride, to be an especially desirable activator. However, we believe our invention is applicable to oligomerization of ethylene by transition metal catalyst systems generally. Since these are well described in the prior art no detailed discussion is necessary here.

The oligomerization of ethylene is a liquid phase reaction, and the catalyst can be either dissolved in a solvent or suspended in a liquid medium. In the variant of particular interest here the catalyst is dissolved in a solvent which is a polar organic liquid. The solvent needs to be inert to process components and apparatus under process conditions. Examples of suitable polar organic liquids as solvents, intended to be representative rather than exclusive, include sulfolane (tetramethylenesulfone), ethylene glycol, 1,4-butanediol, and ethylene carbonate, as well as mixtures of the foregoing. In the variant under discussion here solvents which permit ready phase separation from oligomeric products are preferred in order to have a polar solvent phase and a hydrocarbon phase. The most preferred polar organic liquid as solvent for ethylene oligomerization is sulfolane in which the catalysts of our invention are quite soluble but the oligomers are not.

Oligomerization conditions include a temperature in the range of about 5° C. to about 200° C., with the interval between 20° and 140° C. preferred and that between 40° and about 100° C. even more usual. The process can be run at pressures in the range of about atmospheric pressure to about 5,000 psig, although preferred pressures are in the range of about 400 to about 2,000 psig. These pressures are the pressures at which the ethylene is introduced into the reactor and at which the reactor is maintained. Where ethylene is oligomerized using the catalyst of this invention in the temperature range of 40°–100° C., the optimum water concentration in the polar organic solvent is in the range of 1–6 weight percent.

As commented on above, the oligomerization process forms oligomers which are predominantly linear alpha-olefins having from four to over 20 carbon atoms and which have low solubility in the polar solvents utilized, especially where sulfolane is the solvent for the transition metal catalyst systems of our invention. Consequently, oligomer formation is accompanied by formation of a separate hydrocarbon phase whose constituents are ethylene oligomers with relative proportions closely following a Schulz-Flory distribution. Prior art practice of this invention has included maintaining the water concentration in the polar organic liquid solvent as low as possible, preferably on the order of ppm, but certainly no more than several tenths of a percent water. Our invention is directly contrary to the prior art practice and in fact, constitutes using a polar organic liquid as solvent containing from about 1 up to about 10 wt % water, more preferably between about 2 up to about 5 wt % water, and most preferably from about 3 to about 4 wt % water. We have found that sulfolane containing these amounts of water is a particularly desirable and preferred variant. Where ethylene is oligomerized using the catalysts of this invention in the temperature interval 40°–100° C., the optimum water concentration is in the range from about 1 up to about 6 weight percent.

EXAMPLE 1

Effect of Water on Linear Alpha-Olefin Purity.

A continuous reactor system consisted of a stirred autoclave, containing a solution of sulfolane and catalyst, and a separator. Ethylene was supplied to the reactor at a rate of 160 g/hr at 1500 psig. A mixture of the sulfolane solution, oligomeric product, and unreacted ethylene was conducted from the reactor via a second line to a separator; the sulfolane solution of catalyst was recycled to the reactor and the product/ethylene mixture was drawn off.

The catalyst solution was prepared by adding 1 part by mole of the sodium salt of 2-diphenylphosphino-1-naphthalene sulfonic acid and 2 parts nickel tetrafluoroborate in sulfolane at a total nickel concentration of about 25 ppm Ni. An activator solution of $NaBH_4$ was then added at a ratio of 1 part borohydride to 4 parts nickel. Additional ligand, nickel salt, and activator were added in sulfolane in a 2:4:1 proportion by mole to ensure ethylene conversions in the 10–50 weight percent range. The reaction was conducted at 60° C.

A similar reaction was carried out except that the catalyst solution was prepared by adding 2 parts nickel tetrafluoroborate in a solution of 1 weight percent water in sulfolane and 1 part by mole of the sodium salt of 2-diphenylphosphino-1-naphthalene sulfonic acid with an activator solution of 1 part $NaBH_4$ in dry sulfolane at a total nickel concentration of about 15 ppm. Ligand, nickel salt, and activator were added in 1:2:1 molar proportions in sulfolane containing 1 weight percent water to ensure ethylene conversions in the 10–50 weight percent range.

The purity of linear alpha-olefins formed by oligomerization was assessed by careful analysis of the C10 olefin fraction. In the absence of water the decene fraction was 95.05 weight percent decene-1; in the presence of 0.75 weight percent water the decene fraction was 95.99 weight percent decene-1. The major impurities are tabulated below.

TABLE 1

| Isomers in Decene Fraction (weight percent) | | |
|---|---|---|
| Isomeric decene | 0% $H_2O$ | 0.75% $H_2O$ |
| 7-methylnonene-1 | 0.90 | 0.75 |
| 2-ethyloctene-1 | 0.32 | 0.27 |
| trans-decene-2 | 1.54 | 1.26 |

These results clearly show the beneficial effect of water on olefin purity. This is confirmed by the following data using a similar catalyst system at 3.5 weight percent water. A continuous reactor system consisted of a stirred autoclave, containing a solution of sulfolane and catalyst, and a separator. Ethylene was supplied to the reactor at a rate of 405 g/hr at 1500 psig. The temperature of the reactor was maintained at about 93° C. A mixture of the sulfolane solution, oligomeric product, and unreacted ethylene was conducted from the reactor via a second line to a heated separator; the sulfolane solution of catalyst was recycled to the reactor and the product/ethylene mixture was drawn off. The LAO product and ethylene were subsequently separated and the unreacted ethylene was recycled to the reactor.

The catalyst solution was prepared by adding 2 parts nickel tosylate and 1 part by mole of the sodium salt of 2-butylphenylphosphino-4-methylbenzene sulfonic acid in sulfolane solution containing 3.5 weight percent water with an activator solution of 3 parts $NaBH_4$ at a total nickel concentration of about 25 ppm. Additional ligand, nickel salt, and activator were added in a 1:2:3 proportion by mole in sulfolane containing 3.5 weight percent water to ensure ethylene conversions in the 10–50 weight percent range. Results are summarized in Table 2.

TABLE 2

| Decene-1 Purity in C10 Olefins; 3.5 weight percent water | |
|---|---|
| Ethylene Conversion per pass | Decene-1 purity |
| 10.86 | 96.64 |
| 10.93 | 96.78 |
| 11.59 | 96.45 |
| 13.62 | 96.42 |
| 14.07 | 96.17 |
| 20.69 | 96.19 |
| 22.54 | 96.16 |
| 22.82 | 96.33 |
| 24.45 | 96.30 |

Thus, there is an even greater benefit using water at 3.5 weight percent.

Having demonstrated unequivocally the beneficial effect of added water on alpha-olefin purity, a series of experiments were performed to measure the effect of varying water content on ethylene conversion, its maximum conversion, and on the Schulz-Flory distribution constant.

EXAMPLES 2–5

Effects of Varying Water Concentrations.

The same pilot plant described in Example 1 (no water addition) was operated at 95° C. Ethylene was supplied to the reactor at a rate of 160 g/hr at 1500 psig. The catalyst solution was prepared by adding 2 parts nickel tosylate and 1 part by mole of the sodium salt of 2-butylphenylphosphino4-methylbenzene sulfonic acid in sulfolane solution with an activator solution of 3 parts $NaBH_4$ at a total nickel concentration of about 15 ppm. A variable amount of water in the range of 0.7 to 5 wt % was added to the sulfolane just prior to catalyst addition. The catalyst components were combined over the course of about one hour. The reaction was allowed to proceed with no further catalyst addition until the reaction rate decreased to a negligible level. The ethylene conversion rate was monitored as a function of time after completion of the catalyst addition. The purity and alpha value of the product were also monitored as a function of time. The productivity was calculated by taking the ratio of the total LAO product made during the run and the total ligand added at the start of the run.

TABLE 3

Ethylene Conversion (per pass) as Function of Hours on Stream

| Hours on Stream | 0.71 wt % H₂O | 1.22 wt % H₂O | 2.03 wt % H₂O | 3.23 wt % H₂O | 3.38 wt % H₂O | 4.51 wt % H₂O | 4.76 wt % H₂O |
|---|---|---|---|---|---|---|---|
| 2  | 76.34 | 49.05 | 24.19 | 17.12 | 35.07 | 26.83 | 13.23 |
| 4  | 57.82 | 25.66 | 11.83 | 15.76 | 17.12 | 11.34 | 9.83  |
| 6  | 26.45 | 16.89 | 12.55 | 9.26  | 15.76 | 7.18  | 9.41  |
| 8  | 10.58 | 11.64 | 6.05  | 9.86  | 9.26  | 4.91  | 9.94  |
| 10 | 1.89  | 6.92  |       | 8.77  | 9.86  | 5.29  | 10.58 |
| 12 | 5.29  | 10.32 | 1.74  | 3.17  | 8.77  | 7.94  | 3.97  |
| 14 | 0.38  | 4.50  | 1.89  | 5.56  | 3.17  |       | 4.01  |
| 16 |       | 2.65  | 1.89  |       | 5.56  |       | 0.15  |
| 18 |       | 4.16  | 0.11  |       |       |       | 1.51  |

The foregoing data show that water generally decreases ethylene conversion. A similar conclusion may be reached by comparing ethylene conversion at a constant reaction time, in this case 4 hours on stream, as summarized in Table 4.

TABLE 4

Ethylene Conversion (percent) at 4 Hours on Stream

| Water, weight percent | Maximum conversion weight percent |
|---|---|
| 0.71 | 57.8 |
| 1.22 | 25.7 |
| 2.08 | 11.8 |
| 3.23 | 16.4 |
| 3.38 | 17.1 |
| 4.51 | 11.3 |
| 4.76 | 9.8  |

Note that there appears to be little additional detrimental effect of water on ethylene conversion beyond about 2 weight percent.

Table 5 tabulates the productivity (as defined above) at different water levels.

TABLE 5

Effect of Water Concentration on Productivity

| Water, weight percent | Productivity (g LAO/g ligand) |
|---|---|
| 0.71 | 48,200 |
| 1.22 | 33,100 |
| 2.08 | 14,300 |
| 3.23 | 28,600 |
| 3.38 | 26,300 |
| 4.51 | 16,000 |
| 4.76 | 15,800 |

Once more there appears to be little detrimental effect on productivity beyond about 2 weight percent water.

Table 6 shows the effect of increasing water concentration on the Schulz-Flory distribution.

TABLE 6

Effect of Water Concentration on Schulz-Flory Distribution Constant α

| Water, weight percent | Schulz-Flory α |
|---|---|
| 0.71 | 0.69 |
| 1.22 | 0.68 |
| 2.08 | 0.66 |
| 3.23 | 0.62 |
| 3.38 | 0.63 |
| 4.51 | 0.59 |
| 4.76 | 0.59 |

In contrast to the effect of water on maximum ethylene conversion and productivity, the Schulz-Flory distribution constant appears to decrease throughout the entire range of water concentration used.

What is claimed is:

1. In a process for continuous oligomerization of ethylene to form linear alpha-olefins by contacting, at conditions effective for linear alpha olefin formation, gaseous ethylene with a transition metal catalyst system dissolved in a polar organic liquid, where said transition metal catalyst system is the reaction product of a transition metal compound, a catalyst activator, and an organophosphorus sulfonate ligand, the improvement wherein said polar organic liquid contains from about 1 to about 6 weight percent water.

2. The process of claim 1 where the polar organic liquid is selected from the group consisting of sulfolane, ethylene glycol, 1,4-butanediol, and ethylene carbonate.

3. The process of claim 1 where said polar organic liquid contains from about 2 up to about 5 weight percent water.

4. The process of claim 3 where said polar organic liquid contains from about 3 to about 4 weight percent water.

5. The process of claim 1 where said polar organic liquid is sulfolane.

6. The process of claim 1 where said oligomerization is performed at a temperature from about 5° up to about 200° C. and a pressure between about atmospheric to about 5,000 psig.

7. A process for the continuous oligomerization of ethylene to form linear alpha-olefins using a transition metal catalyst system of the reaction product of a transition metal compound, a catalyst activator, and an organophosphorus sulfonate ligand comprising:

a. introducing ethylene at an oligomerization temperature from about 40° to about 100° C. into a polar phase consisting essentially of a solution of the transition metal catalyst system in an aqueous polar phase of a polar organic liquid phase containing from about 1 up to about 6 weight percent water;

b. oligomerizing ethylene in said aqueous polar phase to afford oligomers consisting essentially of linear alpha-olefins, said oligomers forming a hydrocarbon phase separate from said polar phase; and c. continually withdrawing said hydrocarbon phase.

* * * * *